(12) United States Patent
Bauer et al.

(10) Patent No.: US 12,119,086 B2
(45) Date of Patent: Oct. 15, 2024

(54) METHOD AND SYSTEM FOR PERFORMING DATA ANALYSIS FOR PLANT PHENOTYPING

(71) Applicant: KWS SAAT SE & CO. KGaA, Einbeck (DE)

(72) Inventors: Christoph Bauer, Clausthal-Zellerfeld (DE); Christian Jebsen, Einbeck (DE); Sabine Gubatz, Dassel (DE); Ludmilla Dahl, Einbeck (DE)

(73) Assignee: KWS SAAT SE & CO. KGaA, Einbeck (DE)

( * ) Notice: Subject to any disclaimer, the term of this patent is extended or adjusted under 35 U.S.C. 154(b) by 442 days.

(21) Appl. No.: 16/753,044

(22) PCT Filed: Oct. 4, 2018

(86) PCT No.: PCT/EP2018/077060
§ 371 (c)(1),
(2) Date: Apr. 2, 2020

(87) PCT Pub. No.: WO2019/068835
PCT Pub. Date: Apr. 11, 2019

(65) Prior Publication Data
US 2020/0294620 A1 Sep. 17, 2020

(30) Foreign Application Priority Data
Oct. 4, 2017 (EP) ..................... 17194841

(51) Int. Cl.
*G16B 20/20* (2019.01)
*C12Q 1/6895* (2018.01)
(Continued)

(52) U.S. Cl.
CPC ........... *G16B 20/20* (2019.02); *C12Q 1/6895* (2013.01); *G01N 21/31* (2013.01);
(Continued)

(58) Field of Classification Search
CPC .... G16B 20/20; G01N 21/31; G01N 33/0098; G01N 21/6456; G06V 20/188; G06V 20/194; G06V 2201/10; C12Q 2600/13
See application file for complete search history.

(56) References Cited

U.S. PATENT DOCUMENTS 5,467,271 A * 11/1995 Abel .................... A01B 79/005
702/5
10,031,116 B2 * 7/2018 Geha ....................... G16B 40/00
(Continued)

FOREIGN PATENT DOCUMENTS

CN 106778888 A 5/2017
WO WO-2016069078 A1 * 5/2016 ............... A01H 1/02

OTHER PUBLICATIONS

Sankey et al., UAV lidar and hyperspectral fusion for forest monitoring in the southwestern USA, 2017, Remote Sensing of Environment, 195, 30-43 (Year: 2017).*
(Continued)

*Primary Examiner* — Lori A. Clow
*Assistant Examiner* — Emilie A Neulen
(74) *Attorney, Agent, or Firm* — Troutman Pepper Hamilton Sanders LLP

(57) ABSTRACT

The invention relates to a method for performing data analysis for plant phenotyping of single plants in a field and a data acquisition and evaluation system for performing data analysis for plant phenotyping of single plants in a field. Further, the invention relates to a mobile platform for use in the data acquisition and evaluation system. The method comprises the steps of capturing spectral data via a hyperspectral imaging sensor, capturing image data via an image sensor, capturing georeference data via an inertial measurement unit, spatializing the image data to generate georeferenced image data and a digital surface model, spatializing the spectral data, generating georeferenced spectral data (Continued)

Figure 1:
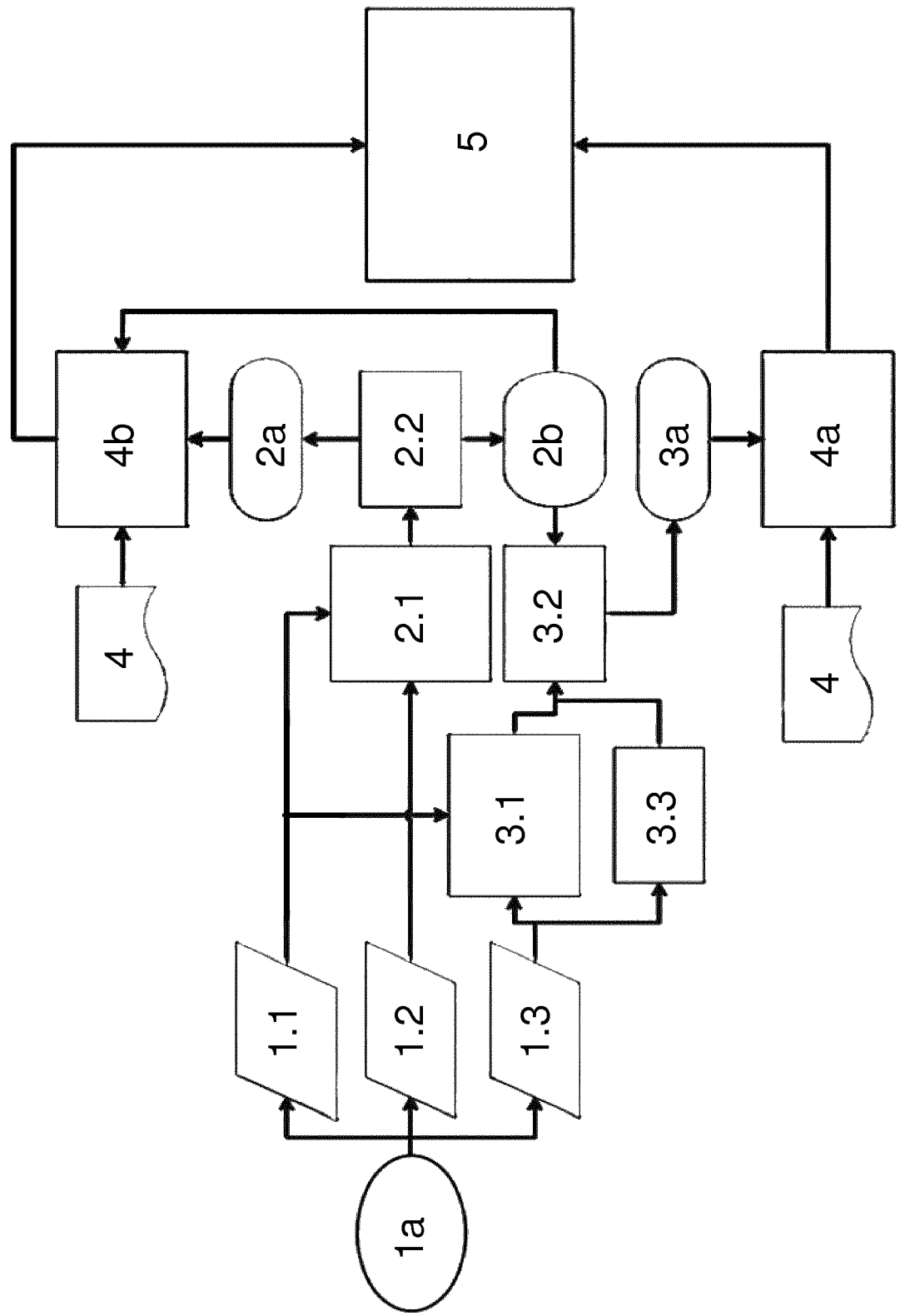

based on the spatialized spectral data and the digital surface model and overlaying the georeferenced image data and georeferenced spectral data with field plan information to generate a high-resolution analysis data set.

27 Claims, 8 Drawing Sheets

(51) Int. Cl.
*G01N 21/31* (2006.01)
*G01N 21/64* (2006.01)
*G01N 33/00* (2006.01)
*G01N 33/24* (2006.01)
*G06V 20/10* (2022.01)
*A01G 7/00* (2006.01)

(52) U.S. Cl.
CPC ....... *G01N 33/0098* (2013.01); *G06V 20/188* (2022.01); *A01G 7/00* (2013.01); *C12Q 2600/13* (2013.01); *C12Q 2600/158* (2013.01); *G01N 21/6456* (2013.01); *G01N 33/245* (2024.05); *G06V 20/194* (2022.01)

(56) References Cited

U.S. PATENT DOCUMENTS

| | | | | |
|---|---|---|---|---|
| RE49,105 E | * | 6/2022 | Smitherman | G01S 19/14 |
| 2009/0271719 A1 | * | 10/2009 | Clare | G09B 29/007 |
| | | | | 715/762 |
| 2015/0015697 A1 | * | 1/2015 | Redden | A01C 21/007 |
| | | | | 382/110 |
| 2016/0205917 A1 | * | 7/2016 | Chan | A01M 21/046 |
| 2020/0033312 A1 | * | 1/2020 | Overton | G01M 5/0091 |

OTHER PUBLICATIONS

Bock, C. H., Poole, G. H., Parker, P. E. and Gottwald, T. R.(2010) 'Plant Disease Severity Estimated Visually, by Digital Photography and Image Analysis, and by Hyperspectral Imaging', Critical Reviews in Plant Sciences, 29: 2, 59-107 (Year: 2010).*

International Search Report and Written Opinion Issued in PCT/EP2018/077060 dated Jan. 28, 2019.

Sankey Temuulen et al., "UAV lidar and Hyperspectral fusion for forest monitoring in the southwestern USA," Remote Sensing of Environment, vol. 195, Apr. 18, 2017, pp. 30-43.

Makynen Jussi et al., Multi- and hyperspectral UAV imaging system for forest and argriculture applications, Next-Generation Spectroscopic Technologies, vol. 8374, No. 1, May 11, 2012, pp. 1-9.

Haghighattalab et al., "Application of unmanned aerial systems for high-throughput phenotyping of large wheat breeding nurseries." Plant Methods 12.1 (2016): 35, 15 pages.

Mahlein et al., "Hyperspectral imaging for small-scale analysis of symptoms caused by different sugar beet diseases." Plant Methods 8.1 (2012): 3, 13 pages.

Jansen et al. "Non-invasive spectral phenotyping methods can improve and accelerate Cercosporasugar beet breeding." Agriculture (2014) 4.2: 147-158.

Suomalainen et al., "A Lightweight Hyperspectral Mapping System and Photogrammertric Processing Chain for Unmanned Aerial Vehicles", Remote Sensing, 2014, vol. 6, No. 11, pp. 11013-11030.

* cited by examiner

METHOD AND SYSTEM FOR PERFORMING DATA ANALYSIS FOR PLANT PHENOTYPING

CROSS-REFERENCE TO RELATED APPLICATIONS

This application is a U.S. National Phase of International Patent Application No. PCT/EP2018/077060, filed on Oct. 4, 2018, which claims priority to European Application No. 17194841.7, filed Oct. 4, 2017. The entire contents of these applications are incorporated herein by reference in their entirety.

The invention relates to a method for performing data analysis for plant phenotyping of single plants in a field and a data acquisition and evaluation system for performing data analysis for plant phenotyping of single plants in a field. Further, the invention relates to a mobile platform for use in said method and/or in said data acquisition and evaluation system and a use of the mobile platform in said method and/or in said data acquisition and evaluation system.

Phenotyping generally relates to a process of measuring, describing and analyzing characteristics of plants like yield, stress resistance (e.g. disease resistance) or herbicide tolerance and is usually carried out in applied plant breeding for a better understanding of gene functions and gene effects, since the genotype and the phenotype often do not correlate directly. A genotype of a plant is a DNA sequence of the genetic makeup determining a phenotype of the plant. The plant phenotype describes observable physical or biochemical characteristics of the plant and is determined by the genotype as well as inherited epigenetic factors and non-inherited environmental influences. Some genes can express a given phenotype in certain environmental conditions. On the contrary, some phenotypes can be the result of several genotypes.

The identification of agronomic traits is usually done by phenotypic selection. Therefore, the traits, which can be determined before harvesting or independent of harvesting, are often estimated by visual rating and collated in a defined grading scale. For this purpose, breeders have to visit numerous trial parcels which are often physically distant or even global distributed. Besides, the phenotyping shall be performed at all trial parcels within a certain period. Therefore, the visual rating has to be carried out in parallel by many different breeders. Due to the subjective nature of the visual rating, grading may differ according to the breeder. The visual rating can often be influenced by different types of visual rating and/or an amount of plants to be evaluated and/or different environmental conditions of the regions in which the plants are grown.

For time reasons and the enormous amount of work, breeders often determine an average grade for one trial plot which comprises numerous plants. A disadvantage is that the visual rating does not allow any conclusion about phenotype differences within the one trial plot. Furthermore, there is no exact measuring, describing and analyzing of characteristics and diseases of single plants.

Another disadvantage is that certain phenotype characteristics cannot be detected visually and/or are dependent on environmental conditions. In particular, insufficient distinct traits, which are often not visually detectable, may be required for genotyping of plants and for gaining a better understanding of the function and effects of genes.

While some prior art methods are able to provide comprehensive information about the traits of analyzed plants, these methods often involve the destruction of the observed plants or part of the plants and often require an amount of work which is time-consuming and cost-intensive.

For instance, low cost unmanned aerial systems are used for rapid proximal measurement of plants and high-resolution measurements for small plot research. Therefore, the low cost unmanned aerial systems comprise an unmanned aerial system platform for data capturing and a three-band multispectral sensor for measuring vegetation indices (see Haghighattalab et al., "Application of unmanned aerial systems for high-throughput phenotyping of large wheat breeding nurseries." Plant methods 12.1 (2016): 35). The data analysis of the low cost unmanned aerial system works semi-automated and the allocation of image data to plot information runs by ground control points.

For laboratory environment, the use of hyperspectral imaging for small-scale analysis of symptoms caused by different sugar beet diseases has been tested (see Mahlein et al., "Hyperspectral imaging for small-scale analysis of symptoms caused by different sugar beet diseases." Plant methods 8.1 (2012): 3). In this method, spectral data have to be captured under artificial and homogenous conditions, for example horizontally fixed leaves to ensure homogenous light conditions. A spectral data analysis has to be performed by a pixel-wise mapping method using disease-specific signatures and spectral angle mapper classification.

Spectrometers of the type FieldSpec and Agricultural Digital Camera are used for manually measurement of Cercospora infestation severity (see Jansen et al. "Non-invasive spectral phenotyping methods can improve and accelerate Cercospora disease scoring in sugar beet breeding." Agriculture 4.2 (2014): 147-158). The analysis of spectra is executed either by estimating the disease severity in pixel ration between NDVI indices values above 0.1 or under 0.1 or by calculating different vegetation indices with spectral information on plot level. This method has the disadvantage that the aimed spectral indices are not disease-specific.

The described prior art methods all have different disadvantages. In particular, the prior art methods are not suitable for a high-throughput and high-resolution phenotyping of single plants in field conditions.

Therefore, it is an object of the present invention to provide a method and a data acquisition and evaluation system for performing data analysis for plant phenotyping of single plants in a field as well as a mobile platform and the use of the mobile platform in said method and/or in said data acquisition and evaluation system, which reduce or eliminate one or more of the above-mentioned disadvantages. In particular, it is an object of the present invention to provide a method and a data acquisition and evaluation system for performing data analysis for plant phenotyping of single plants in a field as well as a mobile platform and the use of the mobile platform in said method and/or in said data acquisition and evaluation system, which enable a reliable and/or time-efficient determination of plant traits.

According to a first aspect of the invention, it is provided a method for performing data analysis for plant phenotyping of single plants in a field, comprising the steps of capturing spectral data via a hyperspectral imaging sensor, capturing image data via an image sensor, capturing georeference data via an inertial measurement unit, preferably via a GNSS aided inertial measurement unit, spatializing the image data to generate georeferenced image data and a digital surface model, spatializing the spectral data, generating georeferenced spectral data based on the spatialized spectral data and the digital surface model and overlaying the georeferenced image data and the georeferenced spectral data with field plan information to generate a high-resolution analysis data set.

The method is suitable for performing data analysis for plant phenotyping of single plants in a field. In particular, the field can be a trial field or a production-scale field for growing numerous plants of one genotype or several genotypes and/or for growing numerous plants of one phenotype or several phenotypes. The production-scale field usually has a size, which is multiple times the size of the trial field, wherein the usually much smaller trial field is used for performing field trials.

Herein, plant phenotyping can also be referred to phenotyping in short. Phenotyping is in particular understood as an overall process for detecting and/or identifying morphological and physical characteristics of plants to determine a phenotype. The phenotype is the composite of observable plant traits, for example a plant height, a plant counting, a row closure, a biomass, fruit/seed yield, leave diseases, insect damages, herbicide tolerance, virus infections by symptoms and abiotic stress effects. For measuring said observable plant traits, the method implies a single plant resolution. Herein, phenotyping preferably comprises performing data analysis, which can include capturing of data and/or further steps of processing data. Further preferably, phenotyping comprises a step of phenotyping analysis. Usually, phenotyping analysis is performed after processing data and/or after generating an analysis data set. Phenotyping analysis can be a final step in phenotyping.

Inter alia, finding a plant phenotype results from an expression of a plant genotype as well as the influence of environmental factors. Therefore, several phenotypes of plants having the same genotype occur due to a location of the field on which the plants are grown. For comparing an influence of the environmental factors, the method described herein provides an automated single plant phenotyping and is preferably a high-throughput process. This has the advantage that the phenotype of single plants of numerous fields which are globally distributed can be detected at the same time and the detected phenotypes can be compared preferably at one main server.

It is particularly preferred to perform data analysis to generate a high-resolution analysis data set for plant phenotyping, in particular data analysis as further detail below. The data analysis principle is based on a process to analyze captured data to allow phenotyping of the single plants, which grow in the field. Therefore, three different sensors are applied for capturing the spectral data, the image data and the georeference data as described hereinafter.

The hyperspectral imaging sensor is intended for capturing the spectral data, the image sensor is intended for capturing the image data and the inertial measurement unit is intended for capturing the georeference data. Herein, the hyperspectral imaging sensor and/or the image sensor and/or the inertial measurement unit may also be referred to as sensor unit(s). Further, herein the hyperspectral imaging sensor and/or the image sensor can preferably be realized as an electro-magnetic sensor.

Preferably, the hyperspectral imaging sensor and/or the image sensor and/or the inertial measurement unit are arranged and/or adapted to capture the data from above. Further preferably, the hyperspectral imaging sensor and/or the image sensor and/or the inertial measurement unit are situated above a canopy of the plants while data capturing, preferably up to 1 m, 2 m, 3 m, 5 m, 10 m, 20 m, 30 m, 40 m, 50 m, 75 m or 100 m above the canopy of the plants. The captured data preferably show the plants from top in a vertical view or a diagonal view from above.

Generally, the method can be used for all crops. The suitability for certain traits is given in particular by the possibility to monitor these traits via sensors by capturing a canopy surface. Therefore, the manifestation of the traits preferably occurs in the canopy of the plants.

In particular, it is preferred that the hyperspectral imaging sensor and/or the image sensor and/or the inertial measurement unit are attached at an underside of a platform, wherein preferably the platform is a mobile platform. The mobile platform is movable, in particular horizontally moveable in parallel of the field ground, wherein its underside facing the field ground.

The hyperspectral imaging sensor collects and processes information from across the electromagnetic spectrum for obtaining the spectrum for each pixel in an image of the field, with the purpose of identifying and detecting plant traits. In particular, the hyperspectral imaging sensor can be integrated into a push broom scanner. The hyperspectral imaging sensor principle is based on dividing images into spectral bands, in particular dividing images into spectral bands that can be extended beyond the visible. Captured spectral data preferably have a high spectral resolution as well as wavelength accuracy and cover a wired range of wavelengths. The hyperspectral imaging sensor preferably measures contiguous spectral bands and captures the plants using a large portion of the electromagnetic spectrum. Typically, the large portion may encompass more than 200 nm, 300 nm, 400 nm, 500 nm, 600 nm, 700 nm, 800 nm, 900 nm or 1000 nm. Often plant traits have unique fingerprints in the electromagnetic spectrum. Known as spectral signatures, these fingerprints enable identification of the plant traits of single plants of the field. It is particularly preferred that the captured spectral data are high-resolution.

The image sensor in particular detects and conveys information that constitutes an image of single plants of the field, preferably by converting the variable attenuation of light waves, preferably visible light waves, into signals, small bursts of current that convey the information. The waves can be light or other electromagnetic radiation. It is particularly preferred that the captured image data are high-resolution.

The inertial measurement unit preferably is a spatial combination of several inertial sensors for motion detection, e.g. accelerate sensors and rotational speed sensors. The inertial measurement unit can also be used for stabilization of the mobile platform. It is particularly preferred that the captured georeference data are high-resolution. In particular, the georeference data can be digital information that can be assigned to a specific location on the field ground, e.g. spatial coordinates (such as GPS coordinates).

After capturing above mentioned data, georectification of the captured spectral data and the captured image data is carried out by spatializing. The captured georeference data are used for merging captured data and allocating the captured data to a field and/or a single plant of the field. Outcomes of spatializing the image data are georeferenced image data and a digital surface model. In particular, the georeferenced image data and a digital surface model are high-resolution. The digital surface model is preferably generated by using an algorithm for combining data of 2D images to 3D images or pseudo 3D images, for example while merging 2D image data to produce a geotiff. In particular, the digital surface model includes some height information describing an orientation and/or direction of growth of the plant and/or its leaves as well as a height of the plant. These height information are particularly preferred for analyzing the spectral data.

The digital surface model is used to spatialize the spectral data for generating georeferenced spectral data. Using the field plan information, the georeferenced image data and/or the georeferenced spectral data can be assigned to the fields, field sectors or even single plants or part of single plants.

A further step comprises overlaying the georeferenced image data and the georeferenced spectral data with the field plan information to generate a high-resolution analysis data set, preferably by using a merging algorithm. Preferably, the georeferenced image data and/or the georeferenced spectral data are high-resolution. The field plan information preferably comprise information for defining field locations and field dimensions, in particular field piece information for defining field piece locations and field piece dimensions. In particular, the step of overlaying the georeferenced image data and the georeferenced spectral data with the field plan information comprises an elimination of interferences which are originated from different background conditions, e.g. sunlight, clouds, temperature, differences in a size, a scale which can be originated from using different lenses and/or sensors as well as changes in physical position.

It is particularly preferred that the field plan information and/or the captured data are high-resolution and as a consequence also the digital surface model and/or the georeferenced spectral data and/or the georeferenced image data. In this way, generating a high-resolution analysis data set is facilitated. In particular, the method can incorporate a highest ground resolution and/or a single plant resolution and/or a geospatial resolution. The high-resolution method allows localizing single plants or parts of single plants, preferably in the range of 25 cm, 20 cm, 15 cm, 10 cm, 5 cm, 3 cm, 2 cm or 1 cm around its real position.

The method has the advantage that the high-resolution data sets are easy to handle and comparable. It also can foster a faster and more effective data analysis. Advantageously, the method is suitable for a high-throughput and standardized procedures.

In particular, the method can further comprise a step of phenotyping analysis. In particular, phenotyping analysis is used to identify plant traits. The step of phenotyping analysis preferably comprises analyzing the high-resolution analysis data set for identifying plant traits.

In addition, the analysis data set and/or the analyzed analysis data assigned to the plant trait can be saved in a database. Further, the generated analysis data set can be automatically assigned to the plant traits by comparing the analysis data set with reference data sets which are saved in the database. In particular, the high-resolution analysis data set can be characterized and plant traits can be determined by means of a database analysis. Preferably, further information of the analysis data can be saved in the database which is used for the database analysis, e.g. location of the field, date, time of the day, time of the year, environmental conditions, etc.

It is a further advantage of the method described herein that the plant traits can be measured quantitatively and analyzed non-destructively. In particular, the combination of the sensor units may identify a color, a size, a shape and/or a temperature of the leaves while a location, a size and/or a plant population are supplied by the field plan information.

In particular, the image sensor is a color sensor. A color sensor can be used for the selective detection and evaluation of the visible spectral range. Such color sensors can be provided for instance in the form of a LAB color sensor, a RGB (red-green-blue) sensor or a true color sensor. The principle of an image of the color sensor is preferably based on a color filter array or a color mosaic array for capturing color information. The color filter filters the light by wavelength range such that separate filtered intensities include information about the color of light.

According to a preferred embodiment, the image sensor is a RGB sensor. The RGB sensor—also called Bayer filter—is an example of above mentioned color filters and gives information about the intensity of light in red, green and blue wavelength regions. A raw image data captured by said RGB Sensor can be converted to a full-color image by a demosaicing algorithm.

Further examples for above mentioned color filters are RGBE filter, CYYM filter, CYGM filter, RGBW Bayer filter, RGBW #1 filter, RGBW #2 filter, RGBW #3 filter or X-Trans filter.

In particular, the image data comprise a plurality of images of at least one field sector, wherein each image comprises a plurality of picture elements. One picture element is preferably one part of image capturing which correspond to one field piece according to high-resolution. Particularly preferred, the plurality of picture elements can be set into grids, e.g. one, two or more lines comprising multiple picture elements. Generally, the field sector can preferably be a part of the field which is captured via one image capturing, wherein the image capturing comprises multiple field pieces and multiple picture elements. Preferably, the field sector can describe one part of the field captured with one image capturing and comprise multiple picture elements.

In a preferred embodiment, spatializing the image data comprises assigning spatial coordinates to the image data and preferably spatially correcting the image data. Thus, spatial information can be assigned to individual image pixels. This embodiment generates high-resolution georeferenced image data for phenotyping of single plants in a field. The spatial correction has the advantage that possible inaccuracies can be corrected to ensure the most accurate spatial information of each individual image pixel.

In particular, spatializing the image data comprises assigning spatial coordinates to the image data and spatially correcting the image data.

It is further preferred that spatializing the spectral data comprises assigning spatial coordinates to spectral data and preferably spatially correcting the spectral data. Thus, spatial information can be assigned to individual spectral image elements. This embodiment generates high-resolution spatialized spectral data for phenotyping of single plants in a field. The spatial correction has the advantage that possible inaccuracies can be corrected to ensure the most accurate spatial information of each spectral image element.

In a further preferred embodiment, spatializing the spectral data comprises a first step of spatializing the spectral data, which comprises assigning spatial coordinates to spectral data and preferably radiometrically correcting the spectral data and preferably a second step of spatializing the spectral data, which comprises spatially correcting the spectral data.

Further preferably, spatializing the spectral data comprises assigning spatial coordinates to spectral data and spatially correcting the spectral data.

It is further preferred that a first step of spatializing the spectral data comprises assigning spatial coordinates to spectral data and radiometrically correcting the spectral data and a second step of spatializing the spectral data comprises spatially correcting the spectral data. Radiometric correction can preferably reduce or corrects radiometric errors or distortions. This process can improve the interpretability and quality of remote sensed data. Radiometric correction is particularly preferred when comparing captured data over a multiple time periods. The emitted or reflected electromagnetic energy from a surface of the field ground that is observed by a sensor onboard mobile platform does not coincide with the energy emitted or reflected from the same surface observed from a short distance because of the sun's azimuth and evaluation and atmospheric conditions. Therefore, in order to obtain the real irradiance or reflectance, it is preferred to correct those radiometric distortions. For instance, radiometric correction can correct effects due to sensor sensitivity, sun angle and topography and/or absorptions and scattering of solar radiation caused by various atmospheric effects.

In a further preferred embodiment, the field plan information comprise field information for defining field locations and field dimensions, in particular field piece information for defining field piece locations and field piece dimensions. In particular, the field plan information has a precision level of +/−0.02 m, 0.03 m, 0.04 m, 0.6 m, 0.8 m, 0.10 m. The field plan information preferably comprises information of field splitting into field pieces, wherein said field pieces have dimensions to ensure capturing high-resolution data. It is preferably preferred that field pieces form a grid of the field.

Preferably, the georeference data and/or the georeferenced image data and/or the georeferenced spectral data comprise georeference coordinates.

In particular, the allocation of captured image data and captured spectral data to field plan information runs automatically by using geolocation data, e.g. from a GPS system.

It is further preferred that overlaying the georeference spectral data and the georeferenced image data with the field plan information comprises an assignment of field piece information according to georeference coordinates. In this way, information of field pieces can be assigned to the captured spectral data and/or the captured image data. The field piece information can be for example an altitude preferably above the sea level, solar hours per day and/or per year, a soil type, etc. Advantageously, these field piece information can be considered in the step of phenotyping analysis.

In a further preferred embodiment, the method comprises the step of capturing additional data via at least one additional sensor, preferably via a thermal sensor and/or an electro-magnetic sensor. In particular, the additional data can additionally or alternatively be captured. In the case of additionally captured additional data, the additional data can be overlaid with the image data, preferably in a way that both images are covering the whole plant in its position, and spatializing said overlaid data to generate the digital surface model and the georeferenced image data. As an alternative or in addition the method can comprise the steps of generating georeferenced additional data by the use of georeference data for spatializing the additional data and overlaying the georeferenced additional data, georeferenced image data and georeferenced spectral data with the field plan information to generate a high-resolution analysis data set.

It can also be preferred that the captured additional data is processed equivalently to the image data. Preferably, captured additional data can be spatialized to georeferenced additional data and a digital surface model. Further, the georeferenced additional data can preferably be overlaid with field plan information and the georeferenced spectral data to generate a high-resolution data set.

It is particularly preferred that the additional sensor is a thermal sensor, preferably an IR (infrared) sensor, for capturing thermal data.

Generally, temperatures of different plant parts or plants compared to their controls are correlated at different time points during development with a genomic database. Merging of image data and thermal data preferably is a segmentation process to separate between plants or parts thereof and background like soil, assign leaves to individual plants and ascertain the quality of infections or drought or osmotic stress.

It can be further preferred that the additional sensor is an electromagnetic sensor, preferably a SWIR (short-wavelength infrared) camera for capturing short waved infrared data.

According to a preferred embodiment, generating the digital surface model comprises multiple recording of an individual picture element by capturing the image data and combining said multiple recorded individual picture elements to a three dimensional image. If applicable—alternatively or additionally—generating the digital surface model can preferably comprise multiple recording of an individual picture element by capturing the additional data and combining said multiple recorded individual picture elements to a three dimensional image.

In particular, multiple recording can describe recording one individual picture element at least double or triple or quadruple or multiple from one perspective in different color and/or wavelength ranges. Alternatively, multiple recording can preferably describe recording one individual picture element at least double or triple or quadruple or multiple from different perspectives. It is preferred that the multiple recording can be made while moving the hyperspectral image sensor and/or the image sensor and/or the inertial measurement unit and/or the additional sensor above the field.

It is particularly preferred, that the three dimensional data image can be produced by merging image data to produce a geotiff, wherein the three dimensional data image can include some height information.

The method preferably comprises the step of using a computer algorithm for phenotyping, in particular phenotyping analysis, that preferably identifies direct traits, leave diseases, insect damages, virus infections by symptoms and/or abiotic stress effects. For example, direct traits can be a plant height, a plant counting, a row closure, a biomass, fruit/seed yield, herbicide tolerance and/or abiotic stress effects can caused by nutrient limitation, environmental temperature, exposure to environmental toxins (e.g. ozone or heavy metals) and/or drought or osmotic stress. It is particularly preferred that the computer algorithm processes the analysis data set by accessing and/or analyzing a database which preferably comprises reference data sets to be able to determine plant traits as well as the phenotype of the plant. Therefore, the computer algorithm is preferably adapted to consider the analysis data set in relation to reference data sets which are stored in the database.

Plant traits of interest are usually defined and demanded by the breeders. After processing data traceability (e.g. correlation, heritability) may be calculated, e.g. correlation of measured and processed data to the plant trait. Data can be evaluated without knowing the plant genotype.

Further preferably, the hyperspectral imaging sensor for capturing spectral data and/or the image sensor for capturing image data and/or the inertial measurement unit for capturing georeference data and/or the additional sensor are arranged on a mobile platform. In particular, it is preferred that one, two, several or all the sensor units are attached at an underside of the mobile platform. The mobile platform is movable, in particular horizontally moveable in parallel of the field ground, wherein its underside facing the field ground. This embodiment has the advantage that data can be captured while moving the mobile platform above the field.

It is particularly preferred that the mobile platform is a ground-based device and/or an aerial device, preferably an autonomous mobile platform. Preferably, an autonomous mobile platform is an unmanned mobile platform and/or can be remote-controlled. This embodiment provides for a particularly easy and time-efficient way to capture data for performing data analysis for plant phenotyping of single plants in a field. In particular, the mobile platform can be moved horizontally in parallel of the field ground, preferably at an altitude up to 1 m, 2 m, 3 m, 5 m, 10 m, 20 m, 30 m, 40 m, 50 m, 75 m or 100 m above the canopy of the plants.

In a preferred embodiment, the hyperspectral imaging sensor for capturing spectral data and/or the image sensor for capturing image data and/or the inertial measurement unit for capturing georeference data and/or the additional sensor are arranged on a mobile platform, wherein the mobile platform is a ground-based device and/or an aerial device, preferably an autonomous mobile platform. The ground-based device can be for example a tractor, a robot or an automat. An example of the aerial device is a drone.

Preferably, the method comprises the step of creating a motion schedule for the autonomous mobile platform. This embodiment provides an automatic motion of the autonomous mobile platform. In particular, a motion path should be straight while a traverse direction of the autonomous mobile platform above the ground should be preferably north to south or south to north. The motion schedule provides preferably that one motion at one timepoint is sufficient for capturing all necessary data. Nevertheless, several measurement timepoints per vegetation period and/or per year can be intended. In particular, the mobile platform can be automatically controlled on the basis of the previously created motion schedule. Therefore, the mobile platform can be preferably connected with a control unit for controlling the movement of the mobile platform.

It is further preferred, that motion data of an actual movement of the mobile platform can be captured during the motion of the mobile platform in accordance with the motion schedule. Actual movement data and the data of the motion schedule can differ, e.g. due to environmental conditions. This preferred embodiment has the advantage that variations can be recognized for being taken into account in the evaluation of the data or for signalizing these variations in such a way as to enable an operator to take control of the movement. Further preferably, the inertial measurement unit is adapted for capturing factual circumstances for comparing said factual circumstances with the considered influencing factors.

In particular, creating the motion schedule should consider several influence factors, which can have a major impact on the high-resolution data. For example, a height, a speed and/or the sensors can be influence factors. Preferably, requirements of the sensor units as well as of the data storage are considered while creating the motion schedule. In order to achieve a ground sampling distance, which enables phenotyping as described herein, the movement of the mobile platform preferably is at an altitude of approximately 2 to 50 meters preferably at an altitude of approximately 25 meters. An optimal altitude of the movement depends on a lens and/or sensor properties, especially on the minimum required focus distance. A resulting size of the analyzed object in a captured image can be a factor limiting distance to the ground. Preferably, when an overlap between two captured data is necessary, determining of the maximum movement speed takes that into account. Another speed-limiting factor can be the integration time of the hyperspectral imaging sensor. Preferably, the integration time is adjusted manually or automatically to the ambient light conditions.

This embodiment is, inter alia, based on the finding that the required ground resolution can depend on the application. The ground resolution can be optimized to a fine ground resolution if very small structures, e.g. single leaves, have to be spatially recognized. In contrast, a lower ground resolution can be sufficient if the spectral information have to be spatially distinguishable on the plot. In consideration of the required ground resolution the speed of the movement can be adjusted.

According to a preferred embodiment, the method comprises pre-processing and/or processing the data on the mobile platform and/or an agricultural station and/or a main server during the operating process and/or in a separate step, which can be offline. Pre-processing can be understood as a part of processing. Processing the data in particular refers to performing data analysis for plant phenotyping. For instance, pre-processing can comprise spatializing the image data to generate georeferenced image data and a digital surface model and/or spatializing the spectral data and/or generating georeferenced spectral data based on the spatialized spectral data and the digital surface. In particular, establishing a relation between a picture element and a position data can be performed in a separate step offline or real time, e.g. by using a real time tracking (turf) algorithm.

It is particularly preferred that the agricultural station can be adapted for pre-processing and/or processing captured data. The agricultural station can be preferably located at the field or in vicinity of the field, wherein the vicinity of the field describe a distance of up to 50 km, 40 km, 30 km, 20 km, 10 km, 5 km or 1 km, preferably a maximum distance to the place of administration of the field. In particular, the agricultural station can comprise a memory unit for storage captured and/or pre-processed and/or processed data and particularly preferred a control unit for pre-processing and/or processing captured data. Further, the control unit can be preferably adapted for controlling the mobile platform. Particularly preferred, the memory unit can be connected with the controlling unit and the mobile platform for storing and accessing the motion schedule.

It is further preferred that the main server can be adapted for processing captured data and/or pre-processed data. The main server can be preferably located at a main location of administration. In particular, the main server can comprise a memory unit for storage of captured and/or pre-processed and/or processed data and particularly preferred a control unit for processing captured data or pre-processed data. Further, the control unit can be preferably adapted for controlling the mobile platform. Particularly preferred, the memory unit can be connected with the controlling unit and the mobile platform for storing and accessing the motion schedule.

In particular, processing captured data can also comprise (further) processing pre-processed data.

Particularly preferred, the method comprises pre-processing and/or processing the data individually for each imaged plant on the mobile platform and/or the agricultural station and/or the main server during the operating process.

Preferably, the mobile platform and/or the agricultural station and/or the main server comprise a memory unit for storing captured data and/or pre-processed data and/or processed data and/or the motion schedule and/or the field plan information.

In a preferred embodiment, the captured data and/or the pre-processed data and/or the processed data are transferred from the mobile platform to the main server and/or from the agricultural station to the main server via a wire connection and/or a wireless connection. Therefore, the mobile platform and/or the agricultural station and/or the main server comprise a wire connection and/or a wireless connection, preferably wlan and/or cable and/or usb and/or Bluetooth™, for transferring the captured data and/or the pre-processed data and/or the processed data from the mobile platform to the agricultural station and/or from the mobile platform to the main server and/or from the agricultural station to the main server.

It is preferably preferred that the mobile platform comprises a memory unit for storing captured data. Preferably, the main server and/or the agricultural station can download said captured data for pre-processing and/or processing. Therefore, the mobile platform and/or the main server and/or the agricultural station comprise an interface, in particular for data transmission, preferably wireless data transmission.

In a preferred embodiment the data can be pre-processed already on the mobile platform during the operating process. In a further preferred embodiment the data can be pre-processed individually for each imaged plant on the mobile platform during the operating process.

According to a further aspect of the invention, it is provided a data acquisition and evaluation system for performing data analysis for plant phenotyping of single plants in a field, comprising a hyperspectral imaging sensor for capturing spectral data, an image sensor for capturing image data, an inertial measurement unit for capturing georeference data and a control unit, which is adapted to spatialize the image data to generate georeferenced image data and a digital surface model, spatialize the spectral data, generate georeferenced spectral data based on the spatialized spectral data and the digital surface model, overlay the georeferenced image data and georeferenced spectral data with field plan information to generate a high-resolution analysis data set.

According to a further aspect of the invention, it is provided a mobile platform using in at least one method and/or in a data acquisition and evaluation system as described herein, comprising a hyperspectral imaging sensor for capturing spectral data, an image sensor for capturing image data and an inertial measurement unit for capturing georeference data. The mobile platform is preferably an autonomous mobile Platform. Preferably, the mobile platform can be an autonomous mobile platform.

According to a further aspect of the invention, it is provided a use of a mobile platform according to a method and/or a data acquisition and evaluation system and/or a mobile platform as described herein.

In any embodiment according to the various aspects of the present invention, the plant may be a plant species selected from the group consisting of: *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia foumieri, Allium cepa, Allium istulosum, Allium sativum,* and *Allium tuberosum.*

According to a further aspect of the invention, it is provided a method for selecting plant, said method comprising: a) growing a plant population; b) performing the above described method for performing data analysis for plant phenotyping of single plants in a field for phenotyping the population of plants based on the high-resolution analysis data set; and selecting a plant from the population having a desired phenotype.

According to a further aspect of the invention, it is provided a method for selecting plant individuals in a breeding program, said method comprising: a) growing a plant population of training individuals; b) performing the above described method for performing data analysis for plant phenotyping of single plants in a field for phenotyping the population of training individuals based on the high-resolution analysis data set and generating a phenotype training data set; c) associating the phenotype training data set with a genotype training data set comprising genetic information across the genome of each training individual to generate an association training data set; d) genotyping a population of breeding individuals; e) selecting breeding pairs from the plant population of breeding individuals based plant genotypes using the association training data set to select breeding pairs likely or able to generate offspring with one or more desired traits; e) optionally, crossing the breeding pairs to generate offspring; and f) optionally, growing the offspring with the one or more desired traits. Preferably, the plant population of training individuals is genetically diverse and/or the plant population of breeding individuals is genetically diverse. The population may include individuals carrying one or more transgenes and/or individuals with DNA edited with random or targeted mutagenesis such as TILLING, preferably combined with chemical mutagens like EMS or ENU, and such as TALEN or CRISPR based modifications as well as base-editor mediated modifications. CRISPR may include in particular CRISPR/Cas9, CRISPR/Cpf1, or CRISPR/Csm1.

In a preferred embodiment, step c) comprises further using a biological model, estimating effects of genotypic markers and linking the estimation of effects of genotypic markers with the biological model to generate an association training data set, and/or step e) comprises using a biological model, estimating effects of genotypic markers and linking the estimation of effects of genotypic markers with the biological model. The incorporation of biological information into such genomic prediction method may allow to reconstruct and predict the target traits such as a complex traits (drought tolerance), which show non-linear relationships among the traits within the parameter estimation process (WO 2016/069078 A1). Traits include, but are not limited to, physiological traits included in crop growth models, individual genes within gene networks, native, gene-edited and transgenic DNA polymorphisms.

Non-limiting examples of traits that can be predicted by the method according to this embodiment are resistance or tolerance to insect pests, such as to rootworms, stem borers, cutworms, beetles, aphids, leafhoppers, weevils, mites and stinkbugs. Other traits can be resistance or tolerance to nematodes, bacterial, fungal or viral pathogens or their vectors. Still other traits could be more efficient nutrient use, such as nitrogen use, and photosynthetic efficiency. Yet other traits could be tolerance to abiotic stressors such as temperature, water supply, salinity, pH, tolerance for extremes in sunlight exposure. Additional traits can be characteristics related to taste, appearance, nutrient or vitamin profiles of edible or feedable portions of the plant, or can be related to the storage longevity or quality of these portions. Finally, traits can be related to agronomic qualities such resistance to lodging, shattering, flowering time, ripening, emergence, harvesting, plant structure, vigor, size, yield, and other characteristics.

In another preferred embodiment of the method, said genotypic information for the candidate is obtained by genotyping using SNP markers and/or by analyses of gene expression, metabolite concentration, or protein concentration.

In another preferred embodiment of the method, the breeding individuals are homozygous or doubled haploids.

According to a further aspect of the invention, it is provided a method for selecting an inbred plant, the method comprising: a) quantitatively assessing the distribution of two or more traits in a population of inbred plants, wherein assessing the distribution of at least one trait is performed by the above described method for performing data analysis for plant phenotyping of single plants in a field; b) constructing a relationship matrix for each inbred plant parent for the two or more traits of interest; c) applying the relationship matrix in a multivariate mixed model analysis for the population of inbred plants; d) obtaining a predicted value for said inbred plant; and e) selecting one or more inbred plants based on the predicted value.

Traits may comprise a plurality of correlated attributes. Preferably the plurality of correlated attributes comprise grain yield, moisture content, total leaf number and/or biomass.

In a preferred embodiment of the method, the population of inbred plants is separated into male and female lines.

In another preferred embodiment, the method further comprises determining the general combining ability and/or the specific combining ability for said plant.

In a further embodiment, the method further comprises calculating a BLUP using the model. Genetic evaluation of a given trait may be described using Best Linear Unbiased Prediction (BLUP). The accuracy of BLUP depends on several factors such as the number of relatives that exists within the population being evaluated, the number of observations made for an individual and/or its relatives, and the variance components of the population. Generally, the more observations that are made for an individual and/or its relatives, the better will be the prediction of its genetic value, and therefore the higher the accuracy of that prediction.

In the genetic evaluation, attributes known to be correlated are seldom analyzed individually. Here, a multivariate mixed model approach is used, with the different attributes analyzed simultaneously. This approach has been shown to provide increase in the accuracy of prediction compared to the univariate approach.

In one embodiment, the method further comprises calculating the accuracy of prediction for each said predicted value.

In another preferred embodiment, the method further comprises selecting a hybrid progeny plant based on predicted values obtained from two parent inbred plants.

As used herein, the term, "accuracy" may generally refer to the correlation between the predicted genetic value (e.g., the BLUP value) and the "true" genetic value, and generally assume a value between 0 and 1. The closer the accuracy is to 1, the close the predicted value is to the true genetic value. In particular embodiments, accuracy in a plant line is determined based on the prediction error variance (PEV) (i.e. the variance of genetic value).

As used herein with regard to traits or attributes, the term "correlated" may refer to a degree or proportion of variance that two traits share due to genetic causes. It may include, for example and without limitation, correlation associated with the proximity of two genes on the same chromosome, or correlation associated with genes that are expressed under the control of common genetic, molecular or environmental factors.

As used herein, the term "general combining ability" may refer to a measure of the value of an inbred line as a parent of a hybrid.

As used herein, the term "mixed-model analysis" may refer to a system which contains experimental factors of both fixed and random-effects types, with appropriately different interpretations and analysis for the two types of factors.

The term "multivariate" may refer to concurrent analysis of two or more variables of interest in an organism. These variables may be associated with a given trait, phenotype, gene, or allele. In some embodiments, these multiple variables may be correlated with each other.

As used herein, the term "specific combining ability" may be used to estimate the value of a parent line (e.g. an inbred parent) to generate a hybrid plant, where the estimation is based on an assessment of the hybrid plant itself. As to the advantages, preferred embodiments and details of these further aspects and their preferred embodiments, reference is made to the corresponding advantages, preferred embodiments and details described above.

Figure 2:
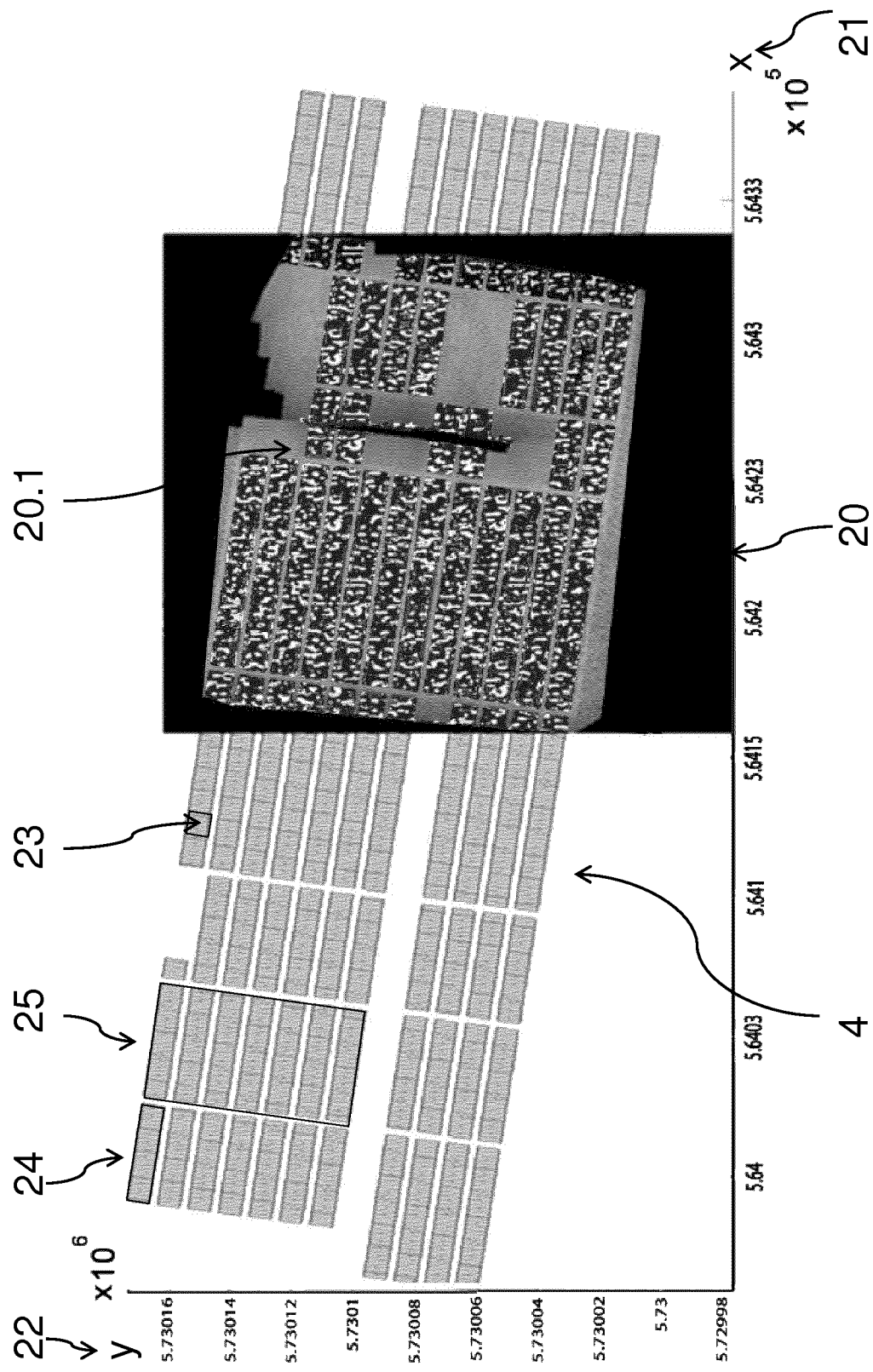
Figure 3:
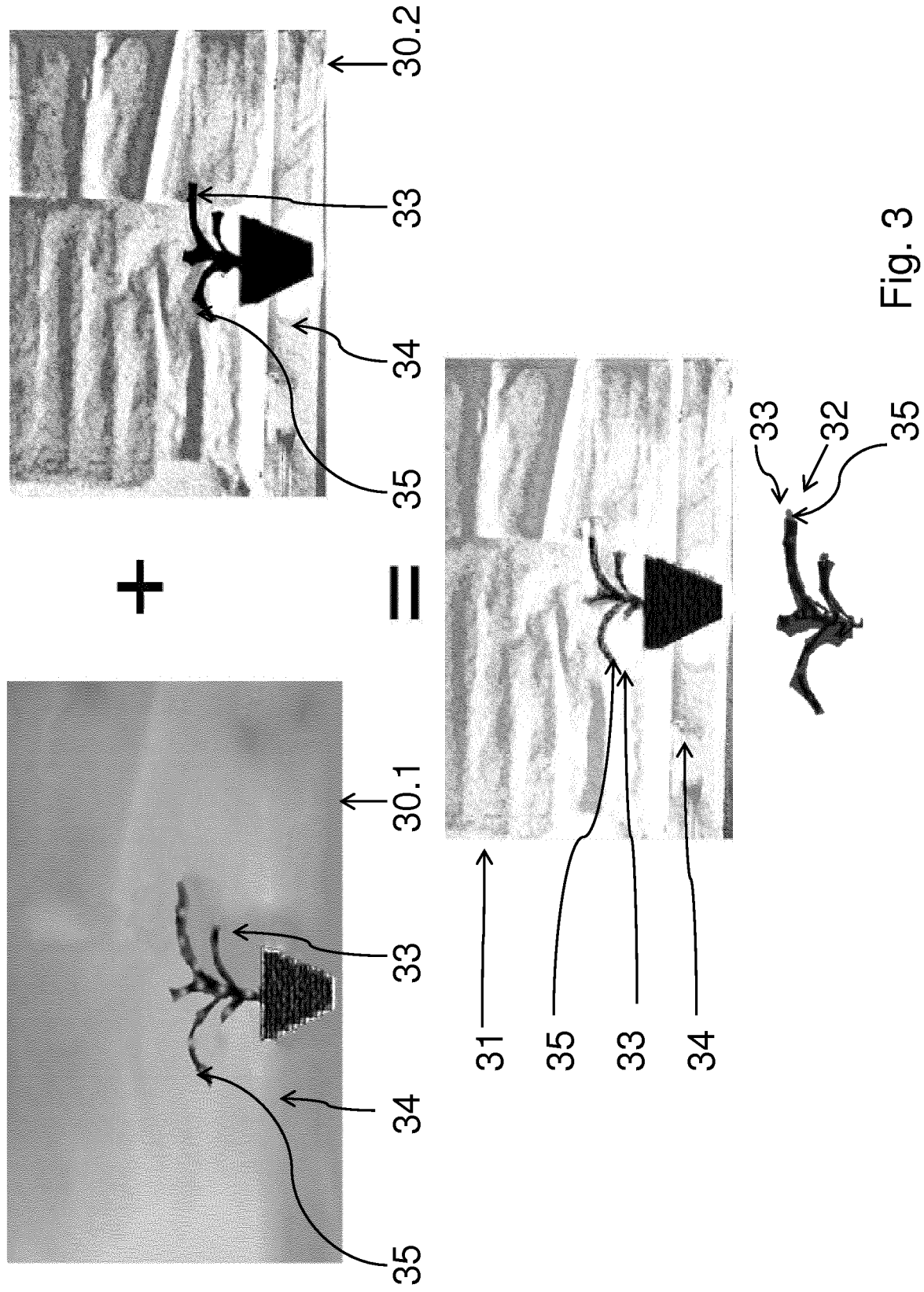
Figure 4:
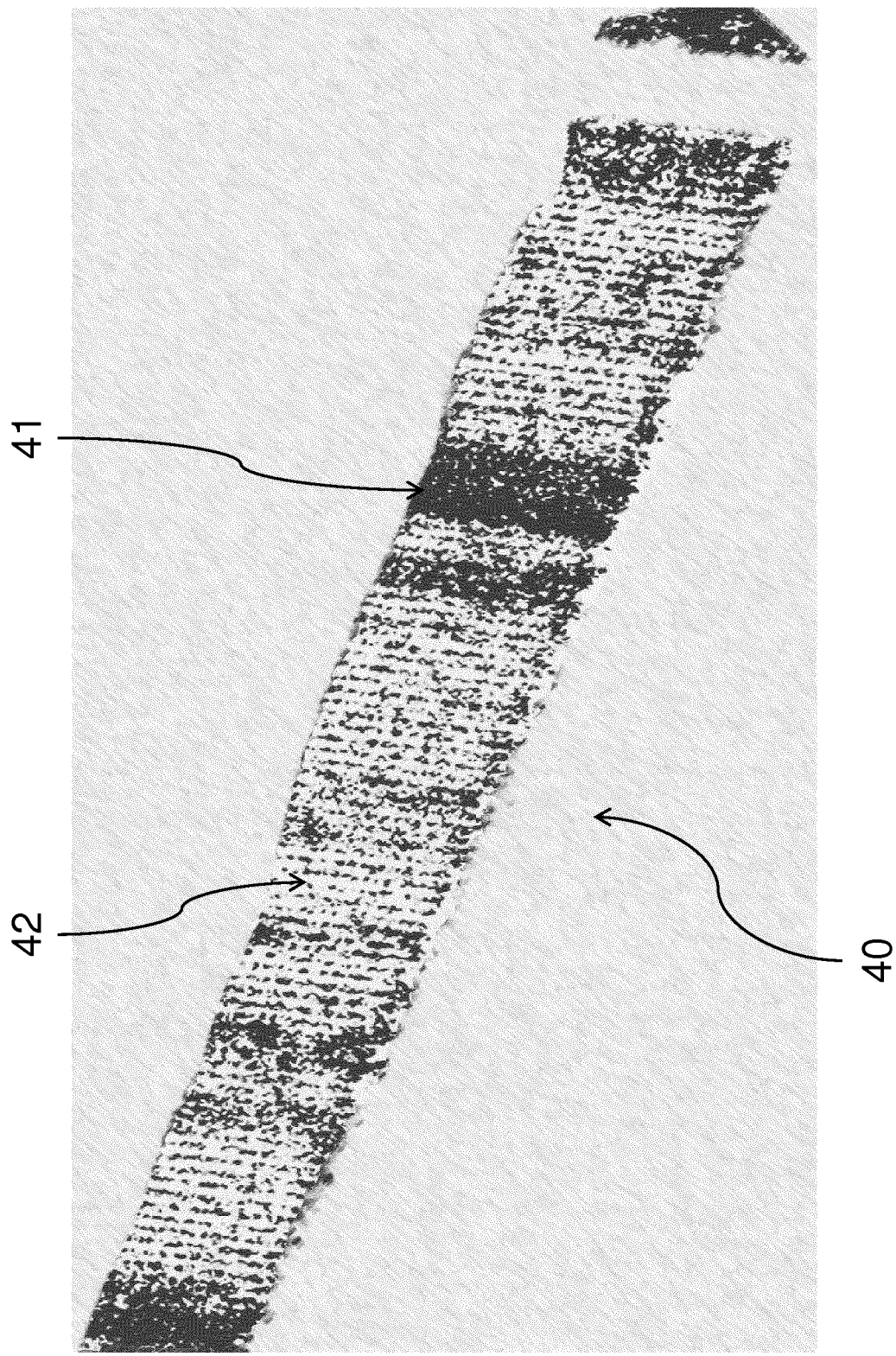
Figure 5A:
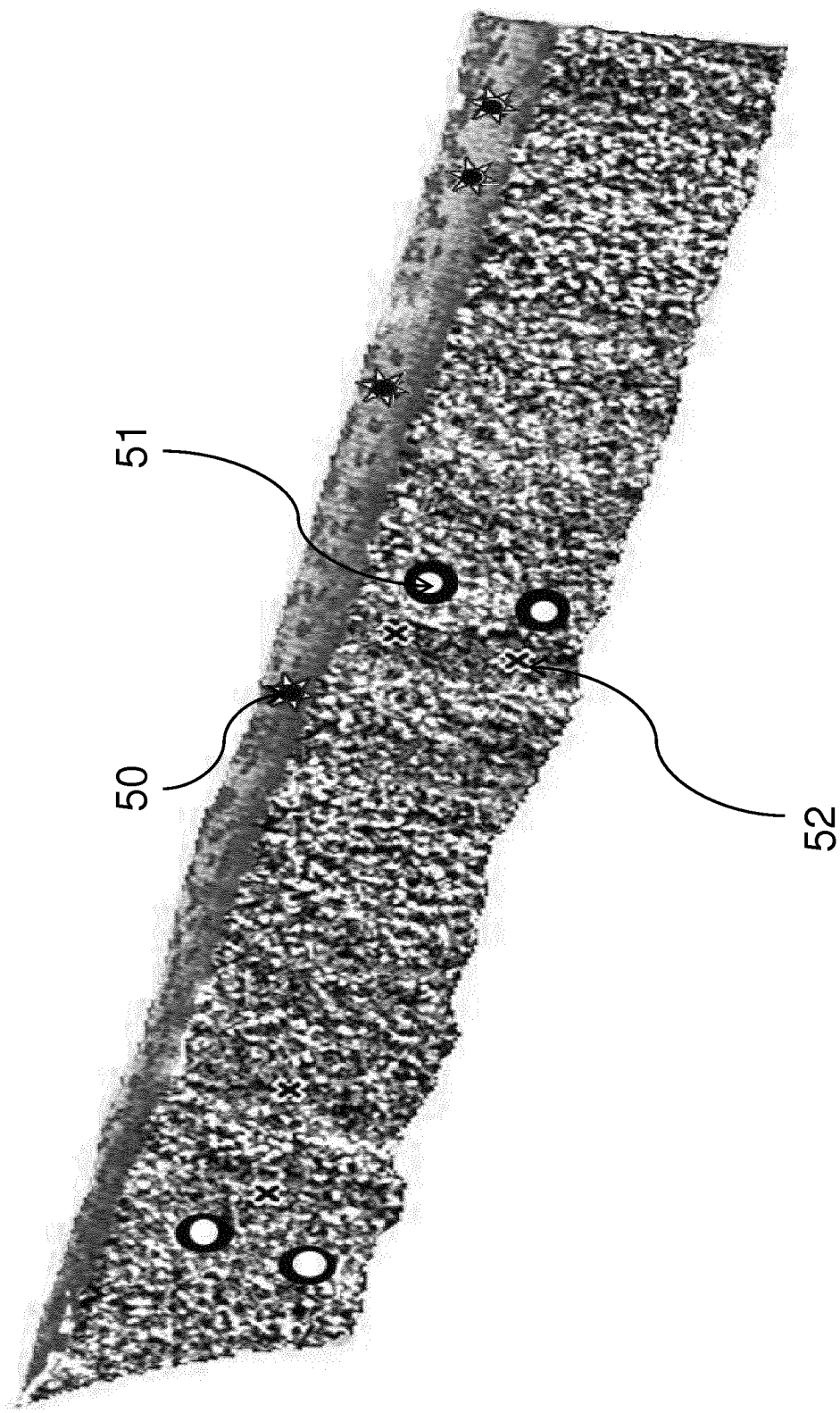
Figure 5B:
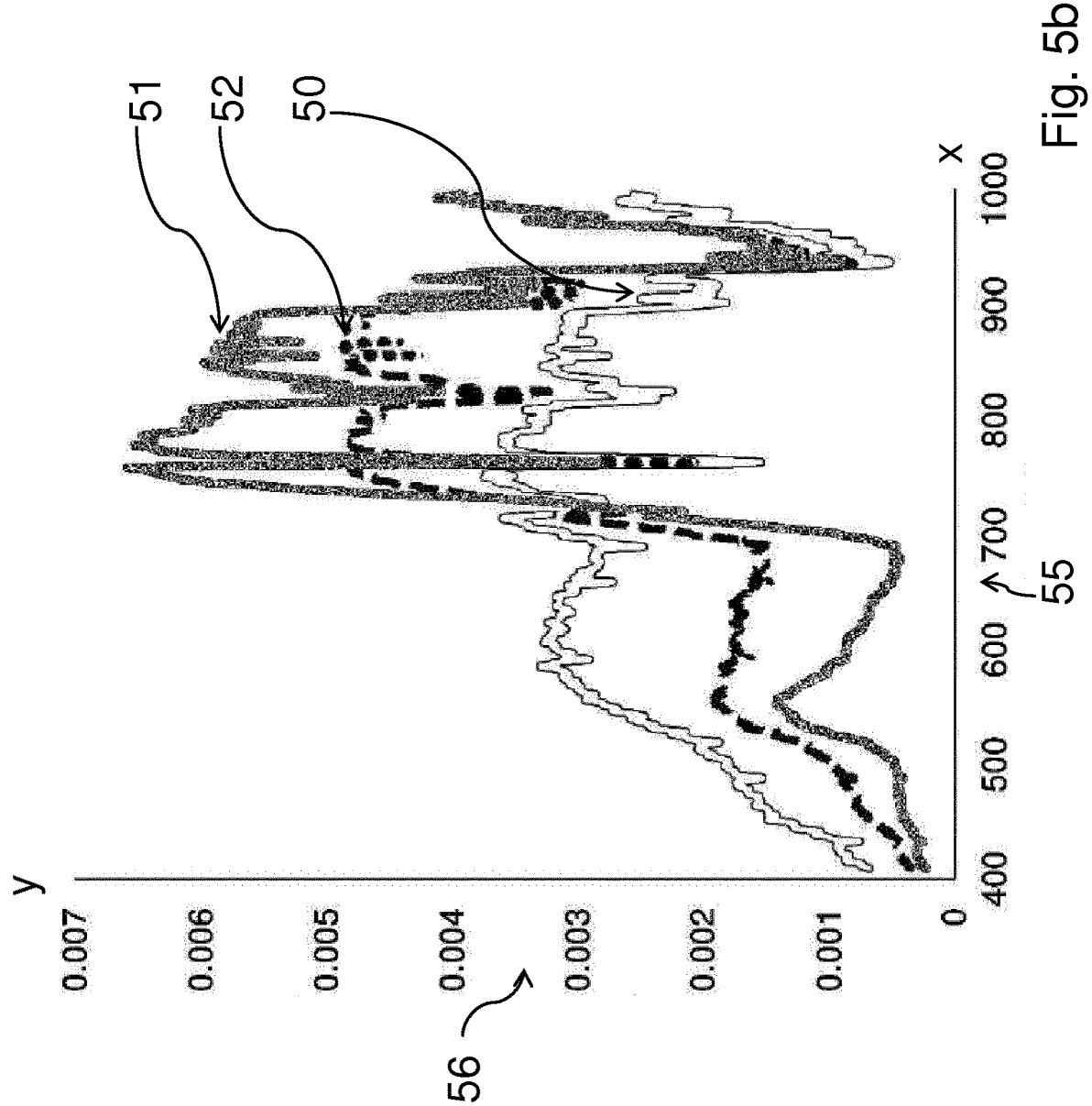
Figure 6:
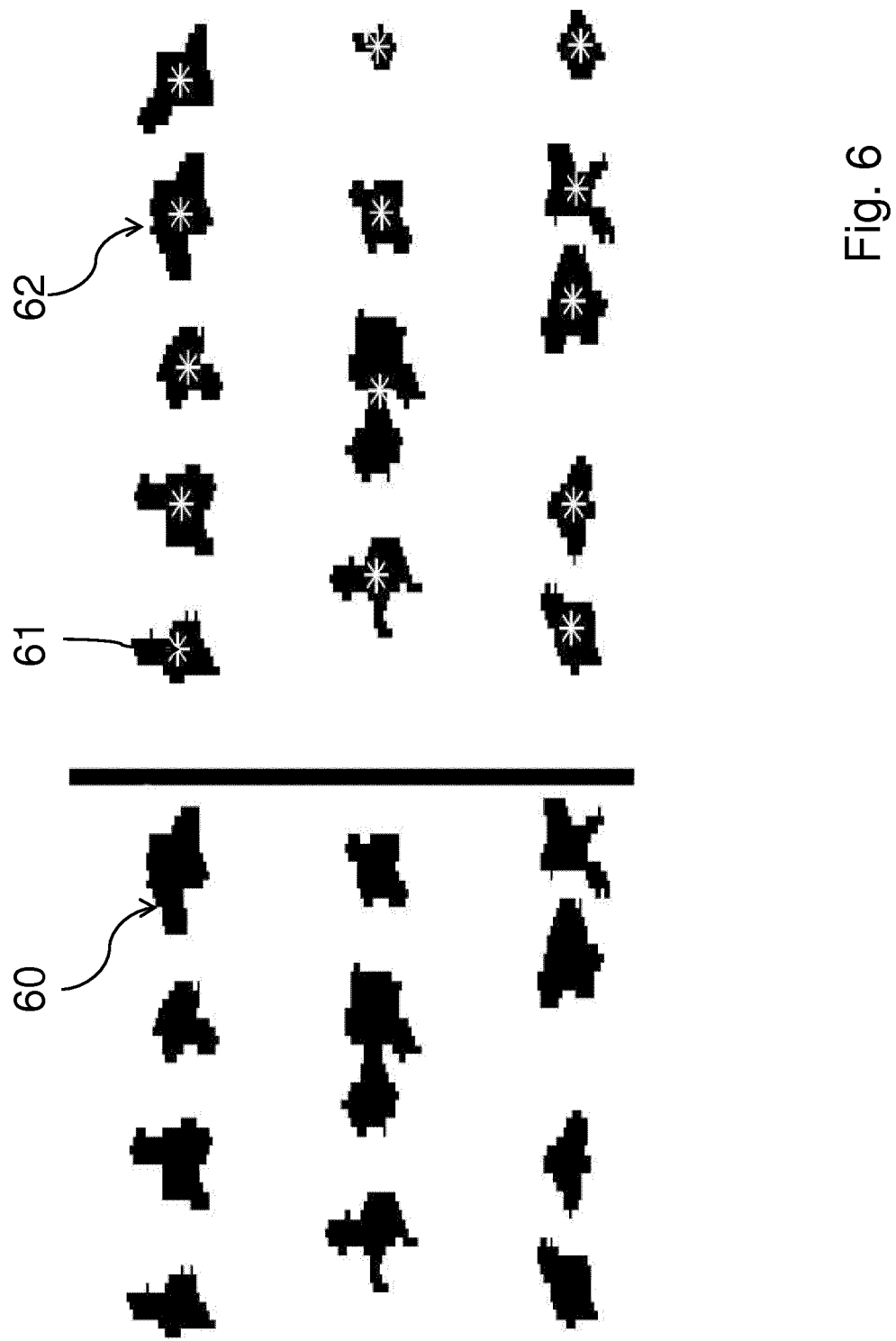

Preferred embodiments of the invention shall now be described with reference to the attached drawings, in which FIG. 1: shows a schematic flow diagram of an exemplary method for performing data analysis for plant phenotyping of single plants in a field;

FIG. 2: shows a geotiff recorded by an aerial device which is overlaid with corresponding field plan information;

FIG. 3: shows merging of captured image data and thermal data;

FIG. 4: shows an example of measurements of a pathogen infection;

FIG. 5A: shows merging of spectral data with RGB data for measuring the pathogen infection according to FIG. 4;

FIG. 5B: shows a spectral comparison of leaf disease, healthy leaf and soil according to FIG. 4 and FIG. 5;

FIG. 6: shows an example for a single plant analysis; and

Figure 7:
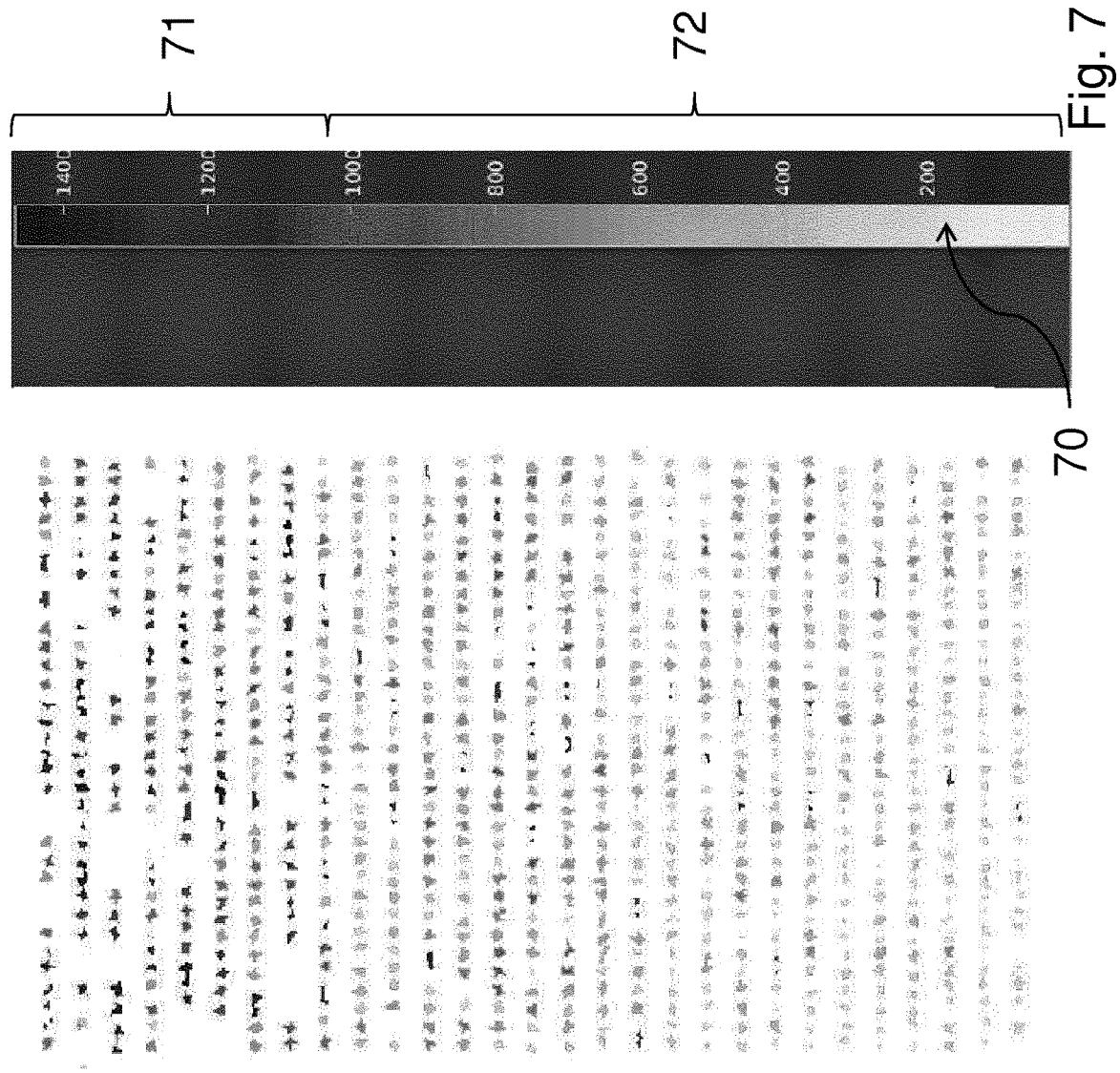

FIG. 7: shows a measurement of leave coverage and/or a biomass.

In the FIGURES, elements with the same or comparable functions are indicated with the same reference numerals.

FIG. 1 shows a schematic flow diagram of the method for performing data analysis for plant phenotyping of single plants in a field is shown. The flow diagram describes the processing of data after capturing these data 1a. The processing can be performed on the mobile platform, an agricultural station and/or a main server. In particular, pre-processing which is a part of processing, can be performed on the mobile platform, wherein the remaining part of processing can be performed on the agricultural station and/or the main server, and/or the agricultural station, wherein the remaining part of processing can be performed on the main server.

The method describes steps of processing after capturing georeference data 1.1 via an inertial measurement unit, image data 1.2 via an image sensor and spectral data 1.3 via a hyperspectral imaging sensor. The first step according to FIG. 1 is spatializing the image data 2.1, 2.2 and spatializing the spectral data 3.1, 3.2, 3.3. Spatializing the image data 2.1, 2.2 comprises assigning spatial coordinates to the image data 2.1 and spatially correcting the image data 2.2 to generate georeferenced image data 2a and a digital surface model 2b by using the georeference data 1.1. Spatializing the spectral data 3.1, 3.2, 3.3 comprises assigning spatial coordinates to spectral data 3.1, a radiometric correction 3.3 and spatial correction 3.2 of the spectral data 1.3. For generating georeferenced spectral data 3a, the spectral data 1.3 where spatialized by using. The next step of the method according to FIG. 1 comprises overlaying the georeferenced image data 2a and the georeferenced spectral data 3a with field plan information 4 to generate a high-resolution analysis data set by assigning of plot information according to geo coordinates 4a, 4b. In a phenotyping analysis 5 the high-resolution analysis data set is analyzed for identifying plant traits. For example, the high-resolution analysis data set can be characterized and plant traits can be determined by means of a database analysis.

FIG. 2 shows a field sector 20.1 in geotiff format 20 recorded by an aerial device, which is overlaid with the corresponding field plan information 4 for analyzing single plants in this field sector 20.1. The field plan information 4 are mapped out as a shapefile defining the plot locations as well as dimensions and cover plots which are not part of the geotiff. Further, axes 21, 22 of the field plan information 4 indicate the north/south and the east/west position of plots and region, which are covered by the image. The scale of the easting axis 21 and the northing axis 22 is meters of a distance to a reference point line. According to FIG. 2, the field plan information 4 define a field splitting into field pieces 23 which have dimensions to ensure capturing high-resolution data. These field pieces 23 form a grid of the field. Further, the field plan information 4 shows blocks 25 which comprise multiple lines 24 of field pieces 23, wherein each line 24 comprises multiple field pieces 23.

As can be seen in FIG. 3, segmentation 32 for separating between a plant 33 and a background 34 can be made by merging captured data. During processing the data captured via different sensor units are preferably merged. Hereby, differences in size, scale often originating from using different lenses and/or sensor units, changes in physical position as well as interferences origination from different environmental conditions, e.g. Sunlight, clouds, temperature, etc., can be eliminated. FIG. 3 shows a thermography 30.1 and a rgb image 30.2 of a maize plant 33 which are merged 31 and segmented 32. This segmentation 32 separates the maize plant 33 from the background 34 to assign leaves 35 of the plant 33 and preferably to ascertain the quality and/or quantity of infections or drought or osmotic stress.

With reference to FIGS. 4, 5a and 5b, a measurement of a pathogen infection is made by merging.

FIG. 4 shows an image of a field 40 after merging captured spectral data and captured RGB data as described above. Due to high ground resolution and known geospatial sensor information it is possible to get information about single plants. The information which are received from one data-capturing-process can be used to setup a time resolved series of the plant and/or trait development during a vegetation period. A visual indication of e.g. different plant traits 41, 42 provides a high-resolution and a less subjective phenotyping analysis. Due to the visual indications, the soil, healthy leaves and leaf diseases can be differentiated. Plant traits as well as the soil often have unique fingerprints in the electromagnetic spectrum. Known as spectral signatures, these fingerprints enable identification of the plant traits of single plants of the field.

In FIG. 5a the soil 50, healthy leaves 51 and leaf diseases 52 are marked. The detection of plant traits can be achieved by comparing each pixel-spectrum with a database, in which reference spectra of different plant traits are deposed. Spectral data allow a differentiation of pixels by its underlying chemical composition. Plants, part of the plants or other targets can show the same visual color while having completely different chemical components, e.g. a brown soil and a brown necrotic leaf tissue.

As can be seen in FIG. 5b, a spectral comparison shows that if a similarity of the spectra is high enough the pixel can be classified as "leaf disease"-pixel. On the contrary, if the similarity of the spectra is not high enough the pixel can be classified as "healthy leaf"-pixel. Therefore, a x-axis 55 scale is wavelength in nm and a y-axis 56 scale is a normalized intensity. After classification of all pixels of a plant and/or a part of the plant, the pixels of "leaf disease" and "healthy leaf" can be used to calculate a ratio describing the amount of infestation.

FIG. 6 shows an example of a single plant analysis. The method captures contours 60 and midpoints 61 of the biomass distribution 62 of single plants. Therefore, the method provides the possibility to measure the biomass for single plants. Further, a growth rate of single plants can be calculated on basis of time series biomass measurements.

With reference to FIG. 7, a leaf coverage and/or biomass can be measured by comparing captured and merged data of single plants in one trial plot with a spectral reference scale 70. The figure shows single plants in different stages of development. In comparison to the lower part of the trial plot 72, the upper part of the trial plot 71 comprises a canopy between neighbored plants which has been partially closed already. The canopy is often an important parameter for plants. Canopy closure, which describes that a gap between neighbored plants is closed, is crucial for weed control because weed plants growing between the plants competes often with the plants for nutrients and sunlight. In this way, the canopy closure can often hamper the growth of weed plants significantly.

LIST OF REFERENCE SIGNS 1a data of a mobile platform
1.1 georeference data
1.2 image data
1.3 spectral data
2.1 assigning spatial coordinates to the image data
2.2 spatially correcting the image data
2a georeferenced image data
2b digital surface model
3.1 assigning spatial coordinates to spectral data
3.2 spatially correcting the spectral data
3.3 radiometric correcting the spectral data
3a georeferenced spectral data
4 field plan information 4a, 4b assigning of plot information according to geo coordinates
5 phenotyping analysis
20 geotiff
20.1 field sector
21 x-axis, easting [m]
22 y-axis, northing [m]
23 field piece
24 line of field pieces 23
25 block
30.1 thermography image
30.2 RGB image
31 merging
32 segmentation
33 plant/maize plant
34 background
35 assigning leaves
40 field
41, 42 plant traits
50 soil
51 healthy leaves
52 leaf diseases
55 x-axis, wavelength in nm
53 y-axis, normalized intensity
60 contours
61 midpoint
62 biomass distribution
70 spectral reference scale, number of pixels
71 the upper part of the trial plot
72 lower part of the trial plot

The invention claimed is:

1. A computer-aided method for performing data analysis for plant phenotyping of one or more single plants in each of a plurality of distributed fields, comprising the steps of:
simultaneously capturing spectral data associated with the one or more single plants in each of the plurality of distributed fields via a hyperspectral imaging sensor;
simultaneously capturing image data associated with the one or more single plants in each of the plurality of distributed fields via an image sensor, wherein the image sensor is a color sensor for selective detection and evaluation of a visible spectral range;
simultaneously capturing high-resolution georeference data associated with the one or more single plants in each of the plurality of distributed fields via an inertial measurement unit comprising acceleration sensors and rotational speed sensors, the high-resolution georeference data comprising georeferenced coordinates;
transmitting the captured spectral data, image data, and high-resolution georeference data to one or more remote servers;
spatializing, via the one or more remote servers, the image data to generate georeferenced image data and a high-resolution digital surface model, wherein spatializing the image data comprises assigning spatial coordinates to the image data and spatially correcting the image data such that spatial information is assigned to individual image pixels, wherein the high-resolution digital surface model includes height information comprising an orientation of growth of a plant, a direction of growth of the plant, a direction of growth of leaves of the plant, a height of the plant, or combinations thereof, wherein generating the high-resolution digital surface model comprises:
obtaining multiple recordings of an individual picture element by capturing the image data; and
combining the multiple recorded picture elements in a three-dimensional image;
generating, via the one or more remote servers, one or more visual indications of diseased leaves, healthy leaves, soil, or combinations thereof from the spectral data by comparing the spectral data to referenced spectral data from a spectral database;
spatializing, via the one or more remote servers, the spectral data;
generating, via the one or more remote servers, georeferenced spectral data from the spatialized spectral data using the high-resolution digital surface model;
overlaying, via the one or more remote servers, the one or more visual indications, the georeferenced image data, and the georeferenced spectral data with field plan information to generate a high-resolution analysis data set by using a merging algorithm, wherein the overlaying of the georeferenced image data and the georeferenced spectral data with the field plan information comprises an assignment of field piece information according to the georeferenced coordinates; and
localizing, via the one or more remote servers, the one or more single plants in a range of 10 cm around one or more real positions of the one or more single plants in each of the plurality of distributed fields.

2. The method according to claim 1, wherein the image sensor is an RGB sensor.

3. The method according to claim 1, wherein spatializing the spectral data comprises:
a first step of spatializing the spectral data, which comprises;
assigning spatial coordinates to spectral data; and
radiometrically correcting the spectral data; and
a second step of spatializing the spectral data, which comprises spatially correcting the spectral data.

4. The method according to claim 1, wherein the field plan information comprises field information for defining field locations and field dimensions, in particular field piece information for defining field piece locations and field piece dimensions.

5. The method according to claim 1 further comprises the step of capturing additional data via at least one additional sensor, via a thermal sensor and/or an electro-magnetic sensor.

6. The method according to claim 1, wherein the method further comprises the step of using a computer algorithm for phenotyping that identifies direct traits and/or leaf diseases and/or insect damages and/or virus infections by symptoms and/or abiotic stress effects.

7. The method according to claim 1, wherein the hyperspectral imaging sensor for capturing spectral data and the image sensor for capturing image data and the inertial measurement unit for capturing georeference data are arranged on a mobile platform, wherein the mobile platform is an aerial device configured to be positioned at an altitude 1-100 meters above a canopy of the one or more single plants in each of the plurality of distributed fields.

8. The method according to claim 7, wherein the method further comprises pre-processing and/or processing the spectral data on the mobile platform and/or an agricultural station and/or a main server during an operating process and/or in a separate step offline.

9. The method according to claim 8, wherein captured data and/or pre-processed data and/or the processed spectral data are transferred from the mobile platform to the main server and/or from the agricultural station to the main server via a wire connection and/or a wireless connection.

10. A mobile platform for use in the method according to claim 1, comprising:
the hyperspectral imaging sensor for capturing spectral data;
the image sensor for capturing image data; and
the inertial measurement unit for capturing georeference data.

11. A data acquisition and evaluation system for performing data analysis for plant phenotyping of one or more single plants in each of a plurality of distributed fields, comprising:
a hyperspectral imaging sensor for simultaneously capturing spectral data associated with the one or more single plants in each of the plurality of distributed fields;
an image sensor for simultaneously capturing image data associated with the one or more single plants in each of the plurality of distributed fields, wherein the image sensor is a color sensor for selective detection and evaluation of a visible spectral range;
an inertial measurement unit comprising acceleration sensors and rotational speed sensors for simultaneously capturing high-resolution georeference data associated with the one or more single plants in each of the plurality of distributed fields, the high-resolution georeference data comprising georeferenced coordinates; and
a control unit, which is remote from the hyperspectral imaging sensor, the image sensor, and the inertial measurement unit, and adapted to:
spatialize the image data to generate georeferenced image data and a high-resolution digital surface model, wherein spatializing the image data comprises assigning spatial coordinates to the image data and spatially correcting the image data, whereby spatial information is assigned to individual image pixels, wherein the high-resolution digital surface model includes height information comprising an orientation of growth of a plant, a direction of growth of the plant, a direction of growth of leaves of the plant, a height of the plant, or combinations thereof, wherein generating the high-resolution digital surface model comprises:
obtaining recordings of multiple individual picture elements by capturing the image data;
combining the recorded multiple individual picture elements in a three-dimensional image;
generating one or more visual indications of diseased leaves, healthy leaves, soil, or combinations thereof from the spectral data by comparing the spectral data to referenced spectral data from a spectral database;
spatialize the spectral data;
generate georeferenced spectral data from the spatialized spectral data using the high-resolution digital surface model;
overlay the one or more visual indications, the georeferenced image data, and georeferenced spectral data with field plan information to generate a high-resolution analysis data set, wherein the overlaying of the georeferenced image data and the georeferenced spectral data with the field plan information comprises an assignment of field piece information according to the georeferenced coordinates; and
localize the one or more single plants in a range of 10 cm around one or more real positions of the one or more single plants in each of the plurality of distributed fields.

12. A mobile platform for use in a data acquisition and evaluation system according claim 11, comprising:
the hyperspectral imaging sensor for capturing spectral data;
the image sensor for capturing image data; and
the inertial measurement unit for capturing georeference data,
wherein the mobile platform is an aerial device configured to be positioned at an altitude 1-100 meters above a canopy of the one or more single plants in each of the plurality of distributed fields.

13. A method for selecting a plant, said method comprising:
a) growing a plant population;
b) simultaneously capturing spectral data associated with one or more single plants in each of a plurality of distributed fields via a hyperspectral imaging sensor;
c) simultaneously capturing image data associated with the one or more single plants in each of the plurality of distributed fields via an image sensor, wherein the image sensor is a color sensor for selective detection and evaluation of a visible spectral range;
d) simultaneously capturing high-resolution georeference data associated with the one or more single plants in each of the plurality of distributed fields via an inertial measurement unit comprising accelerate sensors and rotational speed sensors, the high-resolution georeference data comprising georeference coordinates;
e) transmitting the captured spectral data, image data, and high-resolution georeference data to one or more remote servers;
f) generating, via the one or more remote servers, one or more visual indications of diseased leaves, healthy leaves, soil, or combinations thereof from the spectral data by comparing the spectral data to referenced spectral data from a spectral database;
g) spatializing, via the one or more remote servers, the image data to generate georeferenced image data and a high-resolution digital surface model, wherein spatializing the image data comprises assigning spatial coordinates to the image data and spatially correcting the image data, wherein spatial information is assigned to individual image pixels, wherein the high-resolution digital surface model includes height information comprising an orientation of growth of a plant, a direction of growth of the plant, a direction of growth of the leaves of the plant, a height of the plant, or combinations thereof, wherein generating the high-resolution digital surface model comprises:
obtaining multiple recordings of an individual picture element by capturing the image data; and
combining the recorded multiple individual picture elements in a three-dimensional image;
h) spatializing, via the one or more remote servers, the spectral data;
i) generating, via the one or more remote servers, georeferenced spectral data from the spatialized spectral data using the high-resolution digital surface model;
j) overlaying, via the one or more remote servers, the one or more visual indications, the georeferenced image data, and the georeferenced spectral data with field plan information to generate a high-resolution analysis data set by using a merging algorithm, wherein the overlaying of the georeferenced image data and the georeferenced spectral data with the field plan information comprises an assignment of field piece information according to the georeference coordinates;

k) localizing, via the one or more remote servers, the one or more single plants in a range of 10 cm around one or more real positions of the one or more single plants in each of the plurality of distributed fields; and l) selecting a plant from the plant population having a desired phenotype.

14. A method for selecting plant individuals in a breeding program, said method comprising:

a) growing a plant population of training individuals;

b) simultaneously capturing spectral data associated with one or more single plants in each of a plurality of distributed fields via a hyperspectral imaging sensor;

c) simultaneously capturing image data associated with the one or more single plants in each of the plurality of distributed fields via an image sensor, wherein the image sensor is a color sensor for selective detection and evaluation of a visible spectral range;

d) simultaneously capturing high-resolution georeference data associated with the one or more single plants in each of the plurality of distributed fields via an inertial measurement unit comprising accelerate sensors and rotational speed sensors, the high-resolution georeference data comprising georeference coordinates;

e) transmitting the captured spectral data, image data, and high-resolution georeference data to one or more remote servers;

f) spatializing, via the one or more remote servers, the image data to generate georeferenced image data and a high-resolution digital surface model, wherein spatializing the image data comprises assigning spatial coordinates to the image data and spatially correcting the image data, wherein spatial information is assigned to individual image pixels, wherein the high-resolution digital surface model includes height information comprising an orientation of growth of a plant, a direction of growth of the plant, a direction of growth of the leaves of the plant, a height of the plant, or combinations thereof, wherein generating the high-resolution digital surface model comprises:

obtaining multiple recordings of an individual picture element by capturing the image data; and combining the recorded multiple individual picture elements in a three-dimensional image;

g) generating, via the one or more remote servers, one or more visual indications of diseased leaves, healthy leaves, soil, or combinations thereof from the spectral data by comparing the spectral data to referenced spectral data from a spectral database;

h) spatializing, via the one or more remote servers, the spectral data;

i) generating, via the one or more remote servers, georeferenced spectral data from the spatialized spectral data using the high-resolution digital surface model;

j) overlaying, via the one or more remote servers, the one or more visual indications, the georeferenced image data, and the georeferenced spectral data with field plan information to generate a high-resolution analysis data set by using a merging algorithm, wherein the overlaying of the georeferenced image data and the georeferenced spectral data with the field plan information comprises an assignment of field piece information according to the georeference coordinates;

k) localizing, via the one or more remote servers, the one or more single plants in a range of 10 cm around one or more real positions of the one or more single plants in each of the plurality of distributed fields; and l) generating a phenotype training data set;

m) associating the phenotype training data set with a genotype training data set comprising genetic information across a genome of each training individual;

n) genotyping a population of breeding individuals; and o) selecting breeding pairs from the population of breeding individuals based on plant genotypes using the associated training data set to select breeding pairs likely or able to generate offspring with one or more desired traits.

15. The method of claim 14, wherein said genetic information for a candidate is obtained by genotyping using SNP markers.

16. The method of claim 14, wherein said genetic information for a candidate is obtained by analyses of gene expression, metabolite concentration, or protein concentration.

17. The method of claim 14, further comprising:

crossing the breeding pairs to generate offspring; and growing the offspring with the one or more desired traits, wherein said breeding individuals are homozygous.

18. The method of claim 14, further comprising a genetically diverse population that includes individuals carrying one or more transgenes or a genetically diverse population that includes individuals with DNA edited with random or targeted mutagenesis.

19. The method of claim 14, wherein said plant population of training individuals and/or the population of breeding individuals is genetically diverse.

20. A method for selecting an inbred plant, the method comprising:

a) quantitatively assessing a distribution of two or more traits in a population of inbred plants, wherein assessing the distribution of at least one trait is performed on bases of a high-resolution analysis data set generated by:

simultaneously capturing spectral data associated with one or more single plants in each of a plurality of distributed fields via a hyperspectral imaging sensor;

simultaneously capturing image data associated with the one or more single plants in each of the plurality of distributed fields via an image sensor, wherein the image sensor is a color sensor for selective detection and evaluation of a visible spectral range;

simultaneously capturing high-resolution georeference data associated with the one or more single plants in each of the plurality of distributed fields via an inertial measurement unit comprising acceleration sensors and rotational speed sensors, the high-resolution georeference data comprising georeferenced coordinates;

transmitting the captured spectral data, image data, and high-resolution georeference data to one or more remote servers;

spatializing, via the one or more remote servers, the image data to generate georeferenced image data and a high-resolution digital surface model, wherein spatializing the image data comprises assigning spatial coordinates to the image data and spatially correcting the image data such that spatial information is assigned to individual image pixels, wherein the high-resolution digital surface model includes height information comprising an orientation of growth of a plant, a direction of growth of the plant, a direction of growth of the leaves of the plant, a height of the plant, or combinations thereof, wherein generating the high-resolution digital surface model comprises:

obtaining multiple recordings of an individual picture element by capturing the image data; and combining the multiple recorded picture elements in a three-dimensional image;

generating, via the one or more remote servers, one or more visual indications of diseased leaves, healthy leaves, soil, or combinations thereof from the spectral data by comparing the spectral data to referenced spectra data from a spectral database;

spatializing, via the one or more remote servers, the spectral data;

generating, via the one or more remote servers, georeferenced spectral data from the spatialized spectral data using the high-resolution digital surface model; and overlaying, via the one or more remote servers, the one or more visual indications, the georeferenced image data, and the georeferenced spectral data with field plan information to generate the high-resolution analysis data set by using a merging algorithm, wherein the overlaying of the georeferenced image data and the georeferenced spectral data with the field plan information comprises an assignment of field piece information according to the georeferenced coordinates;

localizing, via the one or more remote servers, the one or more single plants in a range of 10 cm around one or more real positions of the one or more single plants in each of the plurality of distributed fields;

b) constructing a relationship matrix for each inbred plant parent for the two or more traits of interest;

c) applying the relationship matrix in a multivariate mixed model analysis for the population of inbred plants;

d) obtaining a predicted value for said inbred plant; and e) selecting one or more inbred plants based on the predicted value.

21. The method of claim 20, wherein the population of inbred plants is separated into male and female lines.

22. The method of claim 20, wherein the traits comprise a plurality of correlated attributes.

23. The method of claim 22, wherein the plurality of correlated attributes comprises grain yield, moisture content, total leaf number and/or biomass.

24. The method of claim 20, further comprising determining the general combining ability and/or a specific combining ability for said plant.

25. The method of claim 20, further comprising calculating a BLUP using the high-resolution digital surface model.

26. The method of claim 20, further comprising calculating an accuracy of prediction for each said predicted value.

27. The method of claim 20, further comprising selecting a hybrid progeny plant based on predicted values obtained from two parent inbred plants.

* * * * *